United States Patent [19]

Harth et al.

[11] Patent Number: 4,507,270

[45] Date of Patent: Mar. 26, 1985

[54] PROCESS FOR THE PREPARATION OF LEAD AND ZINC CYANURATES

[75] Inventors: Hubert Harth; Martin Witthaus, both of Dusseldorf; Wolfgang Gress, Wuppertal, all of Fed. Rep. of Germany

[73] Assignee: Henkel Kommanditgesellschaft auf Aktien, Düsseldorf-Holthausen, Fed. Rep. of Germany

[21] Appl. No.: 449,672

[22] Filed: Dec. 14, 1982

[30] Foreign Application Priority Data

Jul. 2, 1982 [DE] Fed. Rep. of Germany ....... 3224766

[51] Int. Cl.³ ................................................ C01C 3/00
[52] U.S. Cl. .................................................. 423/365
[58] Field of Search ......................................... 423/365

[56] References Cited

U.S. PATENT DOCUMENTS 4,329,381 5/1982 Eschwey et al. .................. 427/386

FOREIGN PATENT DOCUMENTS 1006489 10/1965 United Kingdom ................ 423/365

OTHER PUBLICATIONS

*Chemical Abstracts,* vol. 89, No. 3, Jul. 17, 1978, 24261z.
*Chemical Abstracts,* vol. 91, No. 9, Aug. 27, 1979, 74572p.

*Primary Examiner*—John Doll
*Assistant Examiner*—Wayne A. Langel
*Attorney, Agent, or Firm*—Hammond & Littell Weissenberger & Dippert

[57] ABSTRACT

Lead and zinc cyanurates are known to be suitable as the active ingredients in corrosion inhibiting coating compositions. The invention provides a simplified method of preparing these compounds by reacting lead or zinc oxide with cyanuric acid in an aqueous paste mixture at a somewhat elevated temperature without requiring the presence of a catalyst while applying a shearing force to said paste mixture.

4 Claims, No Drawings

PROCESS FOR THE PREPARATION OF LEAD AND ZINC CYANURATES

BACKGROUND OF THE INVENTION

The invention concerns a process for the preparation of lead and zinc cyanurates from PbO or ZnO, respectively, and cyanuric acid. The reaction of the respective oxides with cyanuric acid takes place in an aqueous paste mixture without the addition of catalysts.

According to the U.S. Pat. No. 4,329,381, lead and zinc cyanurates are used in corrosion-inhibiting coatings for metal surfaces. They can be prepared according to this patent by suspending lead or zinc oxide and cyanuric acid in boiling water, to which acetic acid must be added as catalyst to accelerate the reaction. The cyanurates precipitate from the aqueous solution and must be filtered, washed and dried.

One disadvantage of this process is the low solids content of these suspensions, which in order to remain stirrable may not exceed a maximum of 14% for zinc cyanurate and 20% for lead cyanurate. This results in high production costs. Secondly, the salt must not contain any foreign ions if they are to be used as corrosion inhibiting coatings. Consequently, an expensive washing process is needed for the removal of acetic acid when added as a catalyst.

OBJECTS OF THE INVENTION

An object of the invention is to provide a simple, improved method for the preparation of the cyanurate salts of lead and/or zinc.

Another object of the invention is to provide a method for the preparation of lead and/or zinc cyanurates by reacting PbO or ZnO with cyanuric acid by forming an aqueous, kneadable paste comprising 10 to 80% by weight water based on the total weight of the paste and subjecting the paste to shearing forces while heating to a temperature of between 50° and 250° C.

A further object of the invention is to provide a method for the preparation of lead and/or zinc cyanurates which requires a minimum of water and which avoids the use of catalysts which would have to be removed from the desired salts before they can be used in corrosion inhibiting compositions.

These and other objects of the invention will become more apparent as the description thereof proceeds.

DESCRIPTION OF THE INVENTION

Surprisingly, it was now found that the lead and zinc cyanurates can also be prepared by adding only enough water to a mixture of the respective oxides and the cyanuric acid to form a kneadable paste and subjecting this paste to the shearing forces of mixing and/or kneading machines with built-in dispersing equipment. Catalysts are not necessary in this case. The reaction is completed more quickly than with the suspension process described in the cited patent.

Accordingly, the invention concerns a process for the preparation of lead and zinc cyanurates by the conversion of PbO or ZnO, respectively, and cyanuric acid in the presence of water, characterized by the fact that PbO or ZnO and cyanuric acid are mixed to form a kneadable paste with a low moisture content of 10 to 80% by weight calculated with regard to the weight of the paste. The paste thus obtained is subjected to shearing forces while heating it to between 50° and 250° C.

The moisture content of the paste should be kept as low as possible and depends on the type of salt to be prepared. In each case, enough water must be added to produce a paste that can be kneaded. The moisture content lies between 10 and 80% weight, calculated with regard to the weight of the paste.

The preferred temperature range for the conversion lies between 100° and 180° C. The pressure is 1 to 10 bar.

Suitable for the preparation of the lead and zinc cyanurates are all machines that produce an sufficient shear force, for example vessels with rotor-stator machines, mixers, blenders and kneaders, Particularly suitable are those machines in which the salts can be brought to essentially dryness after the reaction.

An example of this type of machine are paddle mixers with built-in dispersing equipment such as rod or blade mills. The minimum amount of water removed from the reaction products in the paste requires a very small expenditure of energy to accomplish it.

Cyanuric acid is a tribasic acid so it will be understood that the invention covers the preparation of all its salts, i.e. the neutral, acid and basic salts, of dibasic lead and zinc.

The process according to the invention has the further advantage that no catalyst has to be used for the preparation of the lead and zinc cyanurates. This avoids an expensive procedure for the removal of the catalyst which would otherwise be needed. Furthermore, the desired salts can be obtained in solid form, which eliminates the disadvantage that are found with the prior processes which operate with a low solids content and major amounts of water.

The invention is explained in more detail with the examples.

EXAMPLE 1

A paddle mixer with a built-in rod mill was used to mix 73.3 kg deionized water, 120 kg lead oxide (PbO) and 46.7 kg cyanuric acid. The mixture was heated to between 105° and 110° C., with the consequent rise in pressure to 1.6 bar. The reaction was complete after 2.5 hours. The produced lead cyanurate was then dried in the same apparatus at 40 mbar to a residual moisture of less than 1%. Obtained were 163.2 kg neutral lead cyanurate $Pb_3(C_3N_3O_3)_2.2H_2O$.

EXAMPLE 2

A paddle mixer with built-in blade mill was used to mix 84 kg deionized water, 22 kg zinc oxide (ZnO) and 14.3 kg cyanuric acid. The mixture was heated to between 105° and 110° C., with the consequent rise in pressure to 2.1 bar. The reaction was complete after 2 hours. The obtained basic zinc cyanurate was dried in the same apparatus at 40 mbar to a residual moisture content of less than 1%. Obtained were 36.1 kg basic zinc cyanurate $Zn_3(C_3N_3O_3)_2.2ZnO.3H_2O$.

EXAMPLE 3

A paddle mixer with built-in blade mill was used to mix 50 kg deionized water, 80 kg lead oxide (PbO) and 31.1 kg cyanuric acid. The mixture was heated to between 140° and 150° C., with the consequent rise in pressure to between 5 and 6 bar. The reaction was complete after one hour. The lead cyanurate formed was then dried in the same apparatus at 40 mbar to a residual moisture of less than 1%. 108.1 kg neutral lead cyanurate $Pb_3(C_3N_3O_3)_2.2H_2O$ was obtained.

EXAMPLE 4

A paddle mixer with built-in blade mill was used to mix 85 kg deionized water, 22.3 kg zinc oxide (ZnO) and 14.5 kg cyanuric acid. The mixture was heated to between 140° and 150° C., with the consequent rise in pressure to between 5 and 6 bar. The reaction was complete after one hour. The zinc cyanurate formed was dried in the same apparatus at 40 mbar to a residual moisture content of less than 1%. 36.3 kg basic zinc cyanurate $Zn_2(C_3N_3O_3)_2 \cdot 2ZnO \cdot 3H_2O$ was obtained.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the preparation of lead or zinc cyanurate by the reaction of PbO or ZnO, respectively, with cyanuric acid in the presence of water and in the absence of a catalyst, wherein the PbO or ZnO and cyanuric acid are mixed together with an amount of water sufficient only to form a paste thereof that can be kneaded, the paste having a moisture content of between 10 and 80% by weight, calculated with regard to the paste, and said paste is subjected to shearing forces at a temperature between 50° and 250° C.

2. A process according to claim 1, wherein the reaction takes place at a temperature between 100° and 180° C.

3. A process according to claim 1, wherein said paste is subjected to shearing forces in a mixer, dispersing apparatus, or kneading machine.

4. A process according to claim 1, wherein the mixing and reaction take place in a paddle mixer with built-in rod mill or blade mill.

* * * * *